United States Patent
Dariavach et al.

(10) Patent No.: US 9,134,262 B1
(45) Date of Patent: Sep. 15, 2015

(54) MULTI-CHANNEL CONTAMINANT MEASUREMENT SYSTEM

(71) Applicant: EMC Corporation, Hopkinton, MA (US)

(72) Inventors: Nader G. Dariavach, Middleboro, MA (US); Jin Liang, Southborough, MA (US); Francis W. French, Harvard, MA (US); Paul T. Callahan, Acton, MA (US); Gordon O. Barr, Fall River, MA (US)

(73) Assignee: EMC Corporation, Hopkinton, MA (US)

( * ) Notice: Subject to any disclaimer, the term of this patent is extended or adjusted under 35 U.S.C. 154(b) by 209 days.

(21) Appl. No.: 13/630,271

(22) Filed: Sep. 28, 2012

(51) Int. Cl.
*G01N 27/00* (2006.01)
*G01N 27/02* (2006.01)
*G01N 27/04* (2006.01)

(52) U.S. Cl.
CPC ........................ *G01N 27/00* (2013.01)

(58) Field of Classification Search
CPC .................. G01N 2291/0256; G01N 29/036; G01N 27/00
USPC ............ 422/50, 68.1, 82, 82.01, 98; 73/1.02, 73/1.48–1.55, 1.82, 1.83
See application file for complete search history.

(56) References Cited

U.S. PATENT DOCUMENTS

| 4,953,387 | A | * | 9/1990 | Johnson et al. ............. 73/25.03 |
| 5,571,944 | A | * | 11/1996 | Pfeifer et al. ............... 73/24.04 |
| 6,085,576 | A | * | 7/2000 | Sunshine et al. ............ 73/29.01 |

* cited by examiner

*Primary Examiner* — Paul Hyun
*Assistant Examiner* — Robert Eom
(74) *Attorney, Agent, or Firm* — Brian J. Colandreo; Mark H. Whittenberger; Holland & Knight LLP

(57) ABSTRACT

A multi-channel contaminant sensor includes a first contamination test platform including an exposed first base metal portion that react in a first manner when exposed to one or more airborne contaminates. A second contamination test platform includes an exposed second base metal portion that reacts in a second manner when exposed to the one or more airborne contaminants.

17 Claims, 4 Drawing Sheets

MULTI-CHANNEL CONTAMINANT MEASUREMENT SYSTEM

TECHNICAL FIELD

This disclosure relates to contamination measurement systems and, more particularly, to airborne contamination measurement systems.

BACKGROUND

Storing electronic content is of paramount importance in modern business. Accordingly, various systems may be employed to store such electronic content. Unfortunately, such systems often work in harsh work environments. For example, airborne contaminants such as chlorides, sulfides and oxides often result in the growth of corrosion on critical components (especially those made out of copper).

While various systems have been utilized to determine the presence of airborne contaminants, such systems are often incapable of identifying the particular airborne contaminant (as opposed to just indicating that an airborne contaminant is present).

SUMMARY OF DISCLOSURE

In a first implementation, a multi-channel contaminant sensor includes a first contamination test platform including an exposed first base metal portion that react in a first manner when exposed to one or more airborne contaminates. A second contamination test platform includes an exposed second base metal portion that reacts in a second manner when exposed to the one or more airborne contaminants.

One or more of the following features may be included. An energizing circuit may be configured to excite the first contamination test platform and the second contamination test platform. The energizing circuit may be configured to determine a change in resonant frequency of the first base metal and the second base metal. The energizing circuit may be configured to determine a change in resistivity of the first base metal and the second base metal.

The first contamination test platform may include a protected first base metal portion configured to act as a reference for the first base metal. The second contamination test platform may include a protected second base metal portion configured to act as a reference for the second base metal. A third contamination test platform may include an exposed third base metal portion that reacts in a third manner when exposed to the one or more airborne contaminants. The third contamination test platform may include a protected third base metal portion configured to act as a reference for the third base metal. A fourth contamination test platform may include an exposed fourth base metal portion that reacts in a fourth manner when exposed to the one or more airborne contaminants. The fourth contamination test platform may include a protected fourth base metal portion configured to act as a reference for the fourth base metal.

The energizing circuit may be configured to also excite the third contamination test platform and the fourth contamination test platform. One or more of the base metal portions includes a material chosen from the group consisting of: copper, iron, aluminum and zinc.

In another implementation, a multi-channel contaminant sensor includes a first contamination test platform including an exposed first base metal portion that react in a first manner when exposed to one or more airborne contaminates. A second contamination test platform includes an exposed second base metal portion that reacts in a second manner when exposed to the one or more airborne contaminants. A third contamination test platform includes an exposed third base metal portion that reacts in a third manner when exposed to the one or more airborne contaminants. A fourth contamination test platform includes an exposed fourth base metal portion that reacts in a fourth manner when exposed to the one or more airborne contaminants.

One or more of the following features may be included. An energizing circuit may be configured to excite the first contamination test platform, the second contamination test platform, the third contamination test platform, and the fourth contamination test platform. The energizing circuit may be configured to determine a change in resonant frequency of the first base metal and the second base metal. The energizing circuit may be configured to determine a change in resistivity of the first base metal and the second base metal. One or more of the base metal portions may include a material chosen from the group consisting of: copper, iron, aluminum and zinc.

In another implementation, a multi-channel contaminant sensor includes a first contamination test platform including an exposed copper portion that react in a first manner when exposed to one or more airborne contaminates. A second contamination test platform includes an exposed iron portion that reacts in a second manner when exposed to the one or more airborne contaminants. A third contamination test platform includes an exposed aluminum portion that reacts in a third manner when exposed to the one or more airborne contaminants. A fourth contamination test platform includes an exposed zinc portion that reacts in a fourth manner when exposed to the one or more airborne contaminants. An energizing circuit is configured to excite the first contamination test platform, the second contamination test platform, the third contamination test platform, and the fourth contamination test platform.

One or more of the following features may be included. The energizing circuit may be configured to determine a change in resonant frequency of the first base metal and the second base metal. The energizing circuit may be configured to determine a change in resistivity of the first base metal and the second base metal.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

Figure 1:
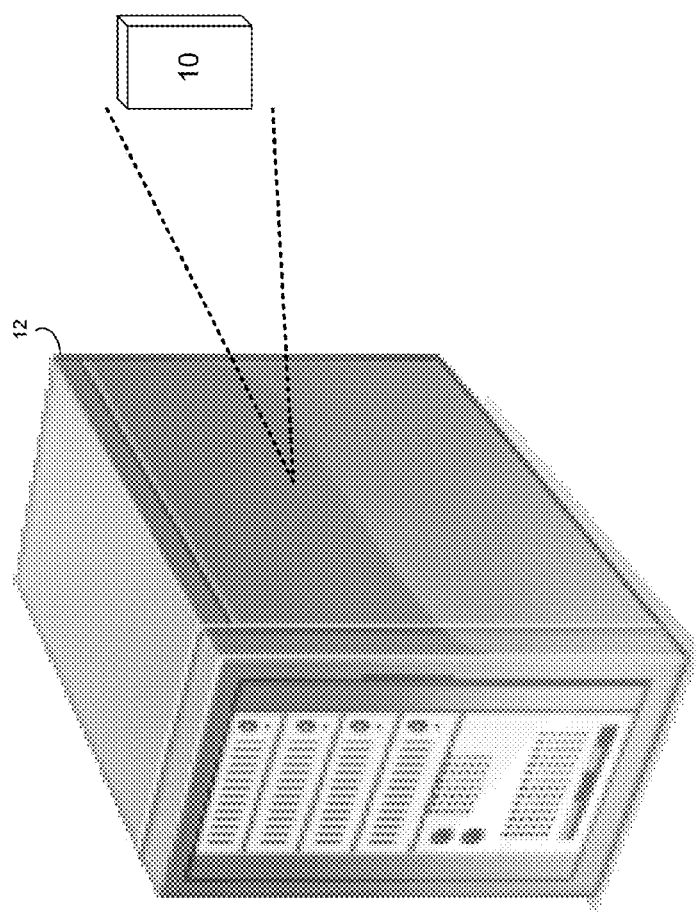
FIG. 1 is a diagrammatic view of a multi-channel contamination measurement system attached to a piece of IT equipment.

Referring to FIG. 1, there is shown multi-channel contamination measurement system 10 that may be positioned within, positioned proximate, or incorporated into IT equipment 12. For example, multi-channel contamination measurement system 10 may be positioned within or proximate one or more server computers, hosts, data arrays, switches, routers, and/or IT equipment racks.

Multi-channel contaminant measurement system 10 may be configured to determine the level of airborne contaminants present within an operating environment (e.g., an IT operating environment). For example, if multi-channel contamination measurement system 10 is incorporated into IT equipment 12, and IT equipment 12 is positioned within a server room (not shown), multi-channel contamination measurement system 10 may measure the quantity of airborne contaminants within the server room (not shown).

As multi-channel contamination measurement system 10 is a multi-channel device, multi-channel contamination measurement system 10 may include at least two contamination test platforms (to be discussed below in greater detail). For the following discussion, multi-channel contamination measurement system 10 is going to be described as including four contamination test platforms. This is for illustrative purposes only and is not intended to be a limitation of this disclosure as the number of test platforms may be increased or decreased in accordance with the needs/performance requirements of multi-channel contamination measurement system 10.

Figure 2:
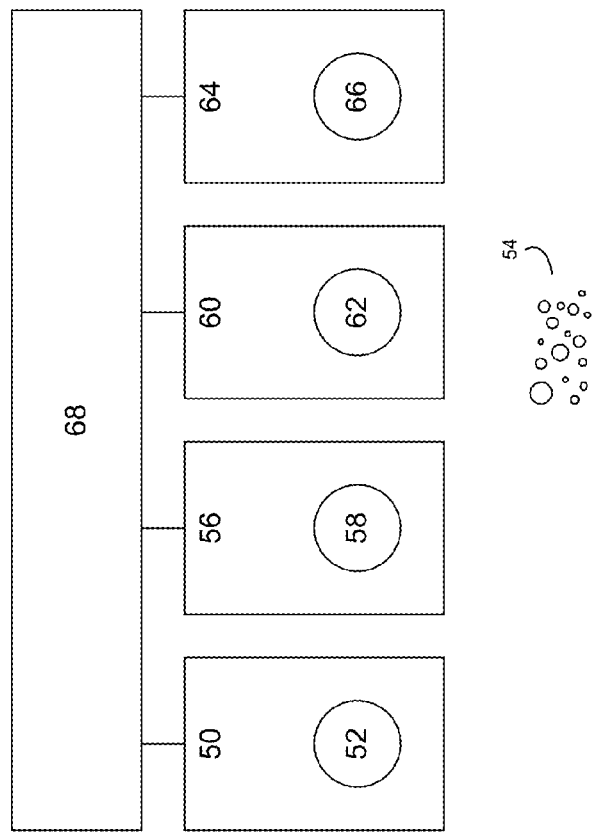
FIG. 2 is a diagrammatic view of the multi-channel contamination measurement system of FIG. 1.

Referring also to FIG. 2 and in one implementation, multi-channel contamination measurement system 10 may include: first contamination test platform 50 including exposed first base metal portion 52 that reacts in a first manner when exposed to one or more airborne contaminates 54; second contamination test platform 56 including exposed second base metal portion 58 that reacts in a second manner when exposed to one or more airborne contaminants 54; third contamination test platform 60 including exposed third base metal portion 62 that reacts in a third manner when exposed to one or more airborne contaminants 54; and fourth contamination test platform 64 including exposed fourth base metal portion 66 that reacts in a fourth manner when exposed to one or more airborne contaminants 54.

One or more of base metal portions 52, 58, 62, 66 includes a material chosen from the group consisting of: copper, iron, aluminum and zinc. For example and in one implementation, multi-channel contamination measurement system 10 includes four separate channels (e.g., test platforms 50, 56, 60, 64), wherein each channel utilizes a different base metal portion. For example, first base metal portion 52 may be constructed of copper, second base metal portion 58 may be constructed of iron, third base metal portion 62 may be constructed of aluminum, and fourth base metal portion 66 may be constructed of zinc. As is known in the art, each of these unique base metals may react differently to the same airborne content. Accordingly, an airborne contaminant that lightly corrodes one base metal may heavily corrode another base metal. Further, by comparing the manner in which each base metal corrodes with respect to the other base metals, a determination may be made concerning what specific contaminants are included within airborne contaminants 54.

Multi-channel contaminant sensor 10 may include energizing circuit 68 that may be configured to excite first contamination test platform 52, second contamination test platform 58, third contamination test platform 62, and fourth contamination test platform 66.

Examples of energizing circuit 68 may include but are not limited to resistivity circuit 100 (see FIG. 3) that may be configured to determine a change in resistivity of the various base metals utilized within multi-channel contamination measurement system 10; and resonant frequency circuit 150 (see FIG. 4) that may be configured to determine a change in resonant frequency of the various base metals utilized within multi-channel contamination measurement system 10.

Figure 3:
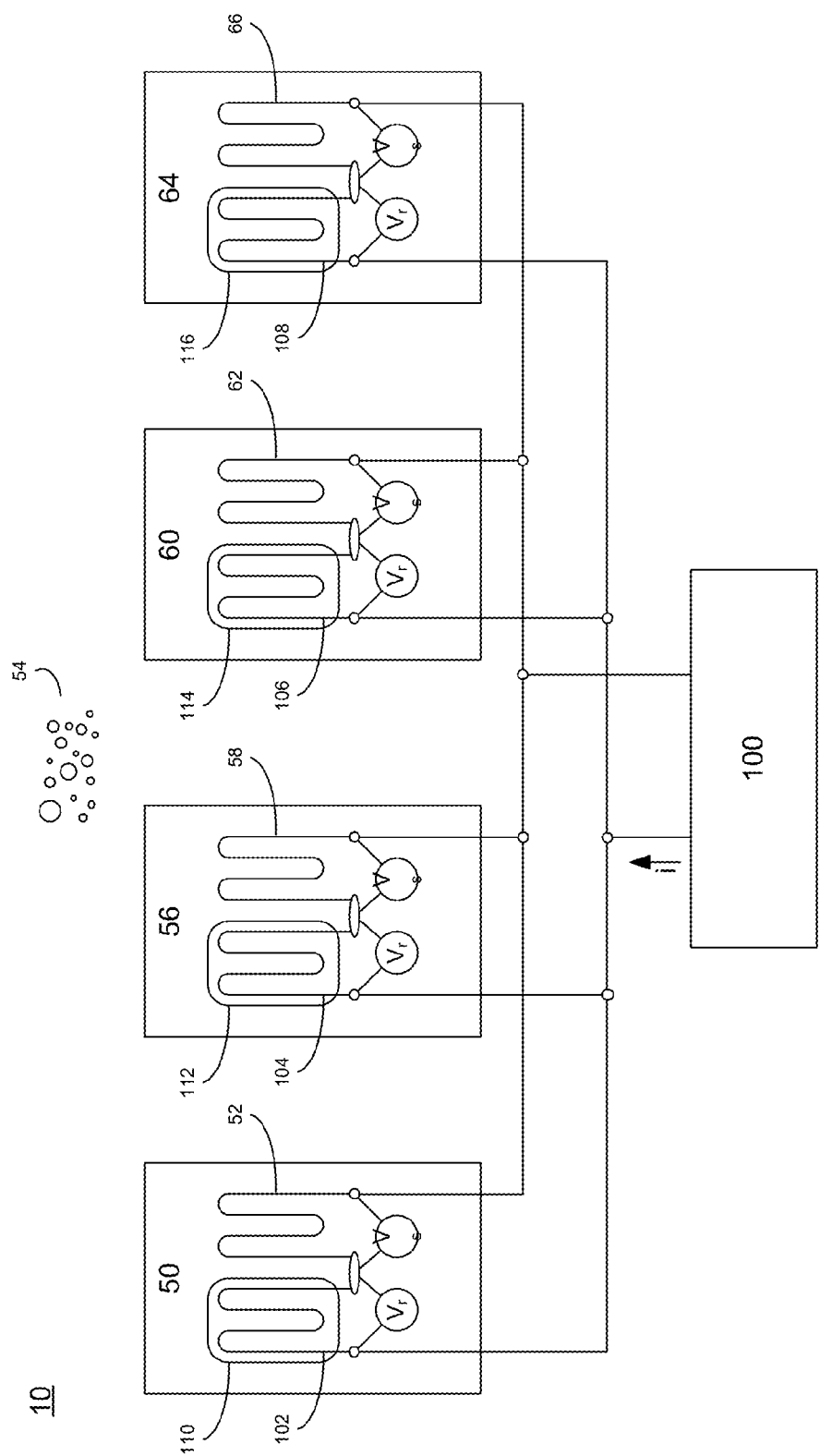
FIG. 3 is a diagrammatic view of the multi-channel contamination measurement system 10 of FIG. 1 including a resistivity circuit.

Referring also to FIG. 3, there is shown one implementation of resistivity circuit 100. In this particular implementation, each of test platforms 50, 56, 60, 64 is shown to include a pair of base metal portions that are configured as metal traces (e.g. metal traces 52, 102 for test platform 50, metal traces 58, 104 for test platform 56, metal traces 62, 106 for test platform 60, and metal traces 66, 108 for test platform 64.

One base metal portion out of each pair of base metal portions included within test platforms 50, 56, 60, 64 may be a protected base metal portion configured to act as a reference base metal portion. Specifically, these protected base metal portions may be covered with a protective layer or film to prevent contamination of the reference base metal portion by airborne contaminants 54.

For example, first contamination test platform 50 may include protected first base metal portion 102 configured to act as a reference for the first base metal. Protected first base metal portion 102 may be covered by protective layer 110 that may be configured to shield first base metal portion 102 from airborne contaminants 54.

Second contamination test platform 56 may include protected second base metal portion 104 configured to act as a reference for the second base metal. Protected second base metal portion 104 may be covered by protective layer 112 that may be configured to shield second base metal portion 104 from airborne contaminants 54.

Third contamination test platform 60 may include protected third base metal portion 106 configured to act as a reference for the third base metal. Protected third base metal portion 106 may be covered by protective layer 114 that may be configured to shield third base metal portion 106 from airborne contaminants 54.

Fourth contamination test platform 64 may include protected fourth base metal portion 108 configured to act as a reference for the fourth base metal. Protected fourth base metal portion 108 may be covered by protective layer 116 that may be configured to shield fourth base metal portion 108 from airborne contaminants 54.

Resistivity circuit 100 may provide a constant current (e.g., current i) to each of test platforms 50, 56, 60, 64. Since each of the pairs of metal traces (e.g., metal traces 52, 110, metal traces 58, 112, metal traces 62, 114, and metal traces 66, 116) are tied together in series, the same current passes through each metal trace in a metal trace pair.

The corrosion depth (CD) on each of the exposed metal traces (namely metal traces 52, 58, 62, 66) may be determined as follows:

$$CD = t_{init}\left(1 - \frac{R_{ref}}{R_{sens}} \frac{R_{sens,init}}{R_{ref,sens}}\right) \text{corrosion depth}$$

| | |
|---|---|
| $t_{init}$ | Initial metal track thickness |
| $R_{sens}$ | Resistance of the sensor track |
| $R_{ref}$ | Resistance of the reference track |
| $R_{sens,init}$, $R_{ref,init}$ | Initial resistance |

Specifically, as metal traces 52, 58, 62, 66 corrode, they get thinner, resulting in an increase in resistivity with respect to the metal trace. Accordingly, by determining the change in resistivity (which may be determined by monitoring the voltage potential across each of the metal trace pairs), the corrosion depth may be determined.

Figure 4:
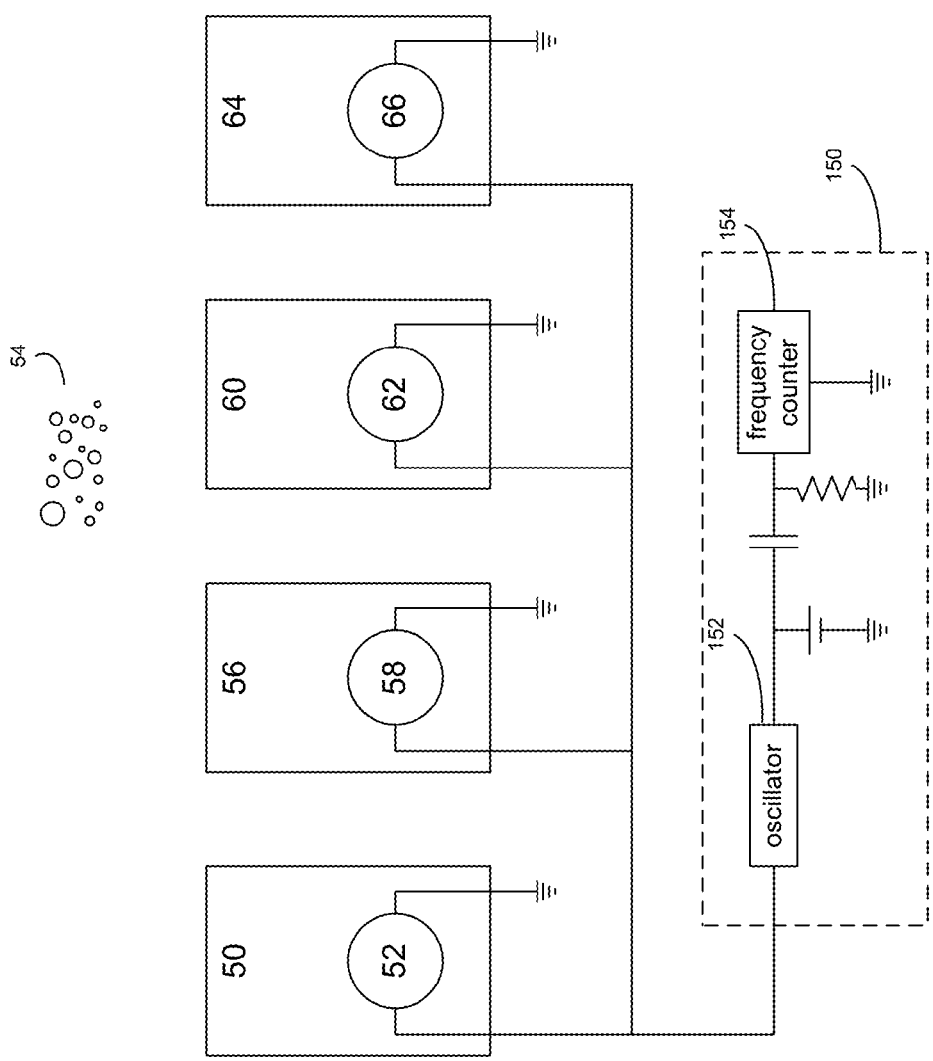
FIG. 4 is a diagrammatic view of the multi-channel contamination measurement system of FIG. 1 including a resonant frequency circuit.

Referring to FIG. 4, there is shown one implementation of resonant frequency circuit 150. As is known in the art, resonant frequency circuit 150 may include oscillator 152, frequency counter 154, and various resistors and capacitors. Each of base metal portions 52, 58, 62, 66 may be constructed of a metallic layer (of e.g., copper, iron, aluminum and/or zinc) disposed upon a ceramic disk. Accordingly and as is known in the art, as a layer of corrosion builds upon base metal portions 52, 58, 62, 66, the weight of the base metal portion (including the corrosion) increases, resulting in a decrease in resonant frequency. Accordingly, by determining the shift in the resonant frequency of a base metal portion, the corrosion depth may be determined as follows:

$$\Delta f = -\left(\frac{f_0^2}{N \cdot \rho_q}\right) \cdot \Delta m$$

$\Delta f$  Change in frequency, resonance frequency
$N$  Frequency constant
$\rho$  Density
$\Delta m$  Mass change/area, assuming film growth on one side of the crystal Accordingly, by using a plurality of base metal portions 52, 58, 62, 66 that each react differently to various types of airborne contaminants, multiple airborne contaminants may be detected via a single multi-channel contaminant sensor 10.

As discussed above, examples of energizing circuit 68 may include but are not limited to resistivity circuit 100 and resonant frequency circuit 150. Resistivity circuit 100 and resonant frequency circuit 150 may be energized periodically (e.g., once per day, per week, per month or per year) to determine the quantity and type of airborne contaminants.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A multi-channel contaminant sensor comprising:
a first contamination test platform including an exposed first base metal portion disposed on the first contamination test platform that reacts in a first manner when exposed to one or more airborne contaminants and a protected first base metal portion disposed on the first contamination test platform configured to act as a reference for a first base metal of the exposed first base metal portion;
a second contamination test platform, separate from the first contamination test platform, including an exposed second base metal portion that reacts in a second manner when exposed to the one or more airborne contaminants; and an energizing circuit configured to determine a corrosion depth associated with one or more of the exposed first base metal portion and the exposed second base metal portion.

2. The multi-channel contaminant sensor of claim 1 wherein the energizing circuit is configured to excite the first contamination test platform and the second contamination test platform.

3. The multi-channel contaminant sensor of claim 2 wherein the energizing circuit is configured to determine a change in resonant frequency of the first base metal and a second base metal of the exposed second base metal portion.

4. The multi-channel contaminant sensor of claim 2 wherein the energizing circuit is configured to determine a change in resistivity of the first base metal and a second base metal of the exposed second base metal portion.

5. The multi-channel contaminant sensor of claim 2 further comprising:
a third contamination test platform including an exposed third base metal portion that reacts in a third manner when exposed to the one or more airborne contaminants.

6. The multi-channel contaminant sensor of claim 5 wherein the third contamination test platform includes a protected third base metal portion, in addition to the exposed third base metal portion, configured to act as a reference for a third base metal of the exposed third base metal portion.

7. The multi-channel contaminant sensor of claim 5 further comprising:
a fourth contamination test platform including an exposed fourth base metal portion that reacts in a fourth manner when exposed to the one or more airborne contaminants.

8. The multi-channel contaminant sensor of claim 7 wherein the fourth contamination test platform includes a protected fourth base metal portion, in addition to the exposed fourth base metal portion, configured to act as a reference for a fourth base metal of the exposed fourth base metal portion.

9. The multi-channel contaminant sensor of claim 7 wherein the energizing circuit is configured to also excite the third contamination test platform and the fourth contamination test platform.

10. The multi-channel contaminant sensor of claim 1 wherein the second contamination test platform includes a protected second base metal portion, in addition to the exposed second base metal portion, configured to act as a reference for a second base metal of the exposed second base metal portion.

11. The multi-channel contaminant sensor of claim 7 wherein one or more of the base metal portions includes a material chosen from the group consisting of: copper, iron, aluminum and zinc.

12. A multi-channel contaminant sensor comprising:
a first contamination test platform including an exposed first base metal portion disposed on the first contamination test platform that reacts in a first manner when exposed to one or more airborne contaminants and a protected first base metal portion configured to act as a reference for a first base metal of the exposed first base metal portion;
a second contamination test platform, separate from the first contamination test platform, including an exposed second base metal portion that reacts in a second manner when exposed to the one or more airborne contaminants;
a third contamination test platform including an exposed third base metal portion that reacts in a third manner when exposed to the one or more airborne contaminants;
a fourth contamination test platform including an exposed fourth base metal portion that reacts in a fourth manner when exposed to the one or more airborne contaminants; and an energizing circuit configured to determine a corrosion depth associated with one or more of the exposed first base metal portion and the exposed second base metal portion.

13. The multi-channel contaminant sensor of claim 12 wherein the energizing circuit is configured to excite the first contamination test platform, the second contamination test platform, the third contamination test platform, and the fourth contamination test platform; and configured to determine a change in resonant frequency of the first base metal and a second base metal of the exposed second base metal portion.

14. The multi-channel contaminant sensor of claim 12 wherein the energizing circuit is configured to excite the first contamination test platform, the second contamination test platform, the third contamination test platform, and the fourth contamination test platform; and configured to determine a change in resistivity of the first base metal and a second base metal of the exposed second base metal portion.

15. A multi-channel contaminant sensor comprising:
   a first contamination test platform including an exposed copper portion disposed on the first contamination test platform that reacts in a first manner when exposed to one or more airborne contaminants;
   a second contamination test platform, separate from the first contamination test platform, including an exposed iron portion disposed on the second contamination test platform that reacts in a second manner when exposed to the one or more airborne contaminants;
   a third contamination test platform including an exposed aluminum portion disposed on the third contamination test platform that reacts in a third manner when exposed to the one or more airborne contaminants;
   a fourth contamination test platform including an exposed zinc portion disposed on the fourth contamination test platform that reacts in a fourth manner when exposed to the one or more airborne contaminants; and
   an energizing circuit which is configured to excite the first contamination test platform, the second contamination test platform, the third contamination test platform, and the fourth contamination test platform;
   wherein each of the contamination test platforms include a protected base metal portion, configured to act as a reference for each contamination test platform, wherein the energizing circuit is configured to determine a corrosion depth associated with one or more of the exposed copper portion and the exposed iron portion.

16. The multi-channel contaminant sensor of claim 15 wherein the energizing circuit is configured to determine a change in resonant frequency of the exposed copper portion and the exposed iron portion.

17. The multi-channel contaminant sensor of claim 15 wherein the energizing circuit is configured to determine a change in resistivity of the exposed copper portion and the exposed iron portion.

* * * * *